United States Patent
Rock

(10) Patent No.: US 9,750,619 B2
(45) Date of Patent: Sep. 5, 2017

(54) SURGICAL INSTRUMENT

(75) Inventor: Michael Rock, Leeds (GB)

(73) Assignee: DEPUY IRELAND UNLIMITED COMPANY, County Cork (IE)

( * ) Notice: Subject to any disclaimer, the term of this patent is extended or adjusted under 35 U.S.C. 154(b) by 314 days.

(21) Appl. No.: 14/343,661

(22) PCT Filed: Aug. 28, 2012

(86) PCT No.: PCT/GB2012/052110
§ 371 (c)(1),
(2), (4) Date: Apr. 3, 2014

(87) PCT Pub. No.: WO2013/034889
PCT Pub. Date: Mar. 14, 2013

(65) Prior Publication Data
US 2014/0228853 A1    Aug. 14, 2014

(30) Foreign Application Priority Data
Sep. 7, 2011    (GB) .................................... 1115411.9

(51) Int. Cl.
*A61F 2/46*    (2006.01)
*A61B 17/17*    (2006.01)
*A61B 17/02*    (2006.01)
*A61B 17/15*    (2006.01)

(52) U.S. Cl.
CPC .......... *A61F 2/4657* (2013.01); *A61B 17/025* (2013.01); *A61B 17/155* (2013.01); *A61B 17/157* (2013.01); *A61B 17/1764* (2013.01); *A61B 2017/0268* (2013.01); *A61F 2002/4658* (2013.01)

(58) Field of Classification Search
CPC .......... A61F 2/46; A61F 2/4657; A61B 17/17; A61B 17/1764
USPC .................... 606/86 R, 87–89, 102
See application file for complete search history.

(56) References Cited

U.S. PATENT DOCUMENTS

| | | |
|---|---|---|
| 3,750,652 A | 8/1973 | Sherwin |
| 4,501,266 A | 2/1985 | McDaniel |
| 4,566,448 A | 1/1986 | Rohr, Jr. |
| 4,898,161 A | 2/1990 | Grundei |

(Continued)

FOREIGN PATENT DOCUMENTS

| | | |
|---|---|---|
| EP | 1348382 A2 | 10/2003 |
| GB | 2198647 A | 6/1998 |

(Continued)

OTHER PUBLICATIONS

PCT International Search Report and Written Opinion PCT/GB2012/052110 dated Dec. 3, 2012.

(Continued)

*Primary Examiner* — Christopher Beccia
(74) *Attorney, Agent, or Firm* — Barnes & Thornburg LLP

(57) ABSTRACT

An adjustable spacer instrument and method of use in a knee arthroplasty procedure are described. The instrument comprises a first member having a substantially planar upper surface and a second member having a substantially planar lower surface. An angular adjustment mechanism is interposed between the first and second members and is operable to adjust the degree of tilt between the upper surface and the lower surface and includes a releasable lock which can maintain the degree of tilt.

20 Claims, 5 Drawing Sheets

(56) References Cited

U.S. PATENT DOCUMENTS

| | | | |
|---|---|---|---|
| 4,938,762 A | 7/1990 | Wehrli | |
| 5,431,653 A | 7/1995 | Callaway | |
| 5,540,696 A | 7/1996 | Booth, Jr. | |
| 5,597,379 A | 1/1997 | Haines | |
| 5,649,929 A | 7/1997 | Callaway | |
| 5,733,292 A | 3/1998 | Gustilo | |
| 5,800,438 A | 9/1998 | Tuke | |
| 5,871,542 A | 2/1999 | Goodfellow et al. | |
| 5,911,723 A | 6/1999 | Ashby | |
| 5,931,777 A | 8/1999 | Sava | |
| 5,989,290 A | 11/1999 | Biedermann | |
| 6,022,377 A * | 2/2000 | Nuelle | A61B 17/025 606/102 |
| 6,159,217 A | 12/2000 | Robie | |
| 6,261,296 B1 | 7/2001 | Aebi | |
| 6,648,896 B2 | 11/2003 | Overes | |
| 6,719,796 B2 * | 4/2004 | Cohen | A61F 2/44 623/17.15 |
| 7,156,853 B2 | 1/2007 | Muratsu | |
| 7,309,363 B2 | 12/2007 | Dietz | |
| 7,976,550 B2 | 7/2011 | Trudeau | |
| 8,137,361 B2 | 3/2012 | Duggineni | |
| 8,197,489 B2 | 6/2012 | Chessar et al. | |
| 8,303,663 B2 | 11/2012 | Jimenez | |
| 9,078,669 B2 | 7/2015 | Dower | |
| 2002/0123754 A1 | 9/2002 | Holmes | |
| 2002/0156480 A1 | 10/2002 | Overes | |
| 2002/0165550 A1 | 11/2002 | Frey | |
| 2003/0225416 A1 | 12/2003 | Bonvallet | |
| 2004/0097951 A1 | 5/2004 | Steffensmeier | |
| 2004/0106927 A1 | 6/2004 | Ruffner | |
| 2004/0122441 A1 | 6/2004 | Muratsu | |
| 2004/0172129 A1 | 9/2004 | Schafer | |
| 2004/0249387 A1 | 12/2004 | Faoro | |
| 2005/0059980 A1 | 3/2005 | Overes | |
| 2005/0085920 A1 | 4/2005 | Williamson | |
| 2005/0177173 A1 | 8/2005 | Aebi | |
| 2006/0074432 A1 | 4/2006 | Stad | |
| 2007/0233144 A1 | 10/2007 | Lavallee | |
| 2007/0239157 A1 | 10/2007 | Guillaume | |
| 2008/0051798 A1 * | 2/2008 | Colquhoun | A61B 17/1764 606/87 |
| 2008/0114367 A1 | 5/2008 | Meyer | |
| 2009/0043310 A1 * | 2/2009 | Rasmussen | A61B 17/025 606/88 |
| 2009/0222089 A1 | 9/2009 | Hauri | |
| 2010/0249789 A1 | 9/2010 | Rock | |
| 2010/0305575 A1 | 12/2010 | Wilkinson et al. | |

FOREIGN PATENT DOCUMENTS

| | | |
|---|---|---|
| WO | WO 9935972 A1 | 7/1999 |
| WO | WO 0019911 A2 | 4/2000 |
| WO | WO 0185038 A8 | 2/2002 |
| WO | WO 02087466 A3 | 2/2003 |
| WO | WO 02071924 B1 | 3/2003 |
| WO | WO 03084412 A1 | 10/2003 |
| WO | 2006136836 A2 | 12/2006 |
| WO | WO 2010116394 A1 | 10/2010 |

OTHER PUBLICATIONS

United Kingdom Search Report GB1115411.9 dated Dec. 8, 2011.
International Search Report, dated Dec. 11, 2006, (10 Pages).
UK Search Report, dated Jan. 25, 2006, (4 Pages).
LCS Complete Mobile-Bearing Knee System, Surgical Technique, 3M1001, 0611-63-050 (Rev. 2), 2001 (44 Pages).
AMK Congruency Instrument System, Surgical Technique, 2.7M1198, 0612-76-000, 1997 (16 Pages).
Knee Balancer Complementing PFC Sigma and LCS Complete EGF Instrumentation, Reference Guide and Surgical Technique, 4M0703, 0612-21-500, 2003 (15 pages).
PCT International Search Report for International App. No. PCT/GB2011/050540, dated Jul. 4, 2011 (12 Pages).
UK Search Report GB1006173.7, dated Aug. 12, 2010 (3 Pages).
NJ LCS® Unicompartmental Knee System with Porocoat®, Surgical Procedure by Frederick F. Buechel, M.D., Biomedical Engineering Trust, South Orange NJ, 1994, (11 Pages).
Rand, James A., M.D., Total Knee Arthroplasty, 1993 by Mayo Foundation, Raven Press, New York, 1993, (8 Pages).
New Jersey LCS® Total Knee System, Surgical Technique, Using Milestone™ Instruments, R. Barry Sorrells, M.D. and Frederick F. Buechel, M.D., DePuy, 20MO104, 0601-87, 1994, (57 Pages).
Letter and Subsequently Filed Items in European Patent Application No. 12756236.1, filed Oct. 21, 2014.

* cited by examiner

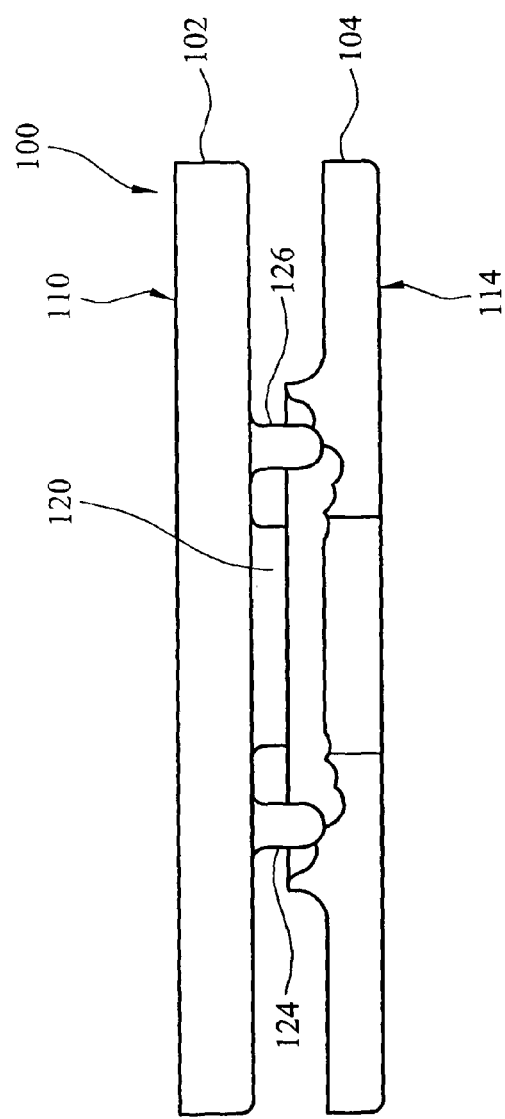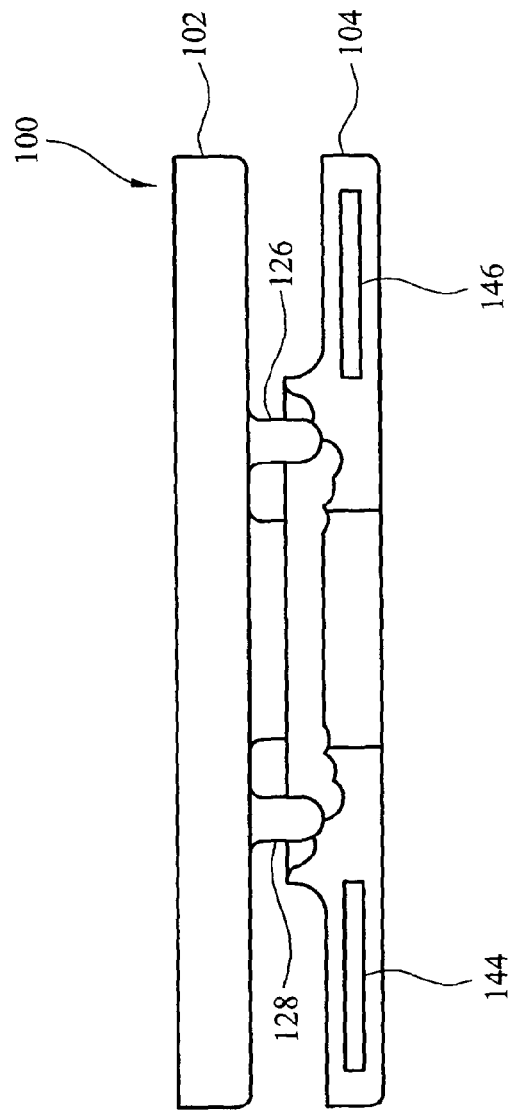

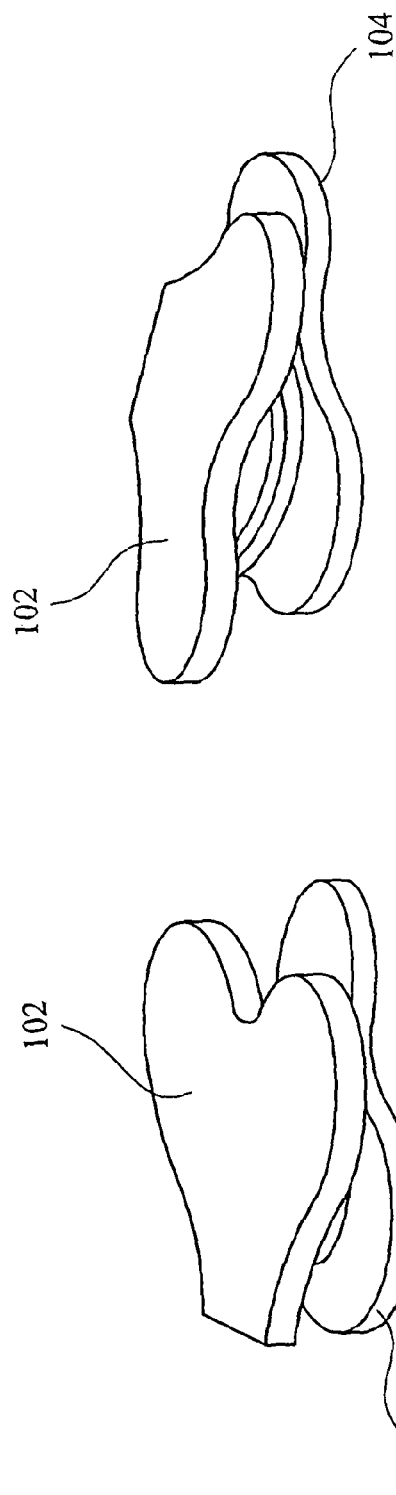
FIG. 5
FIG. 7
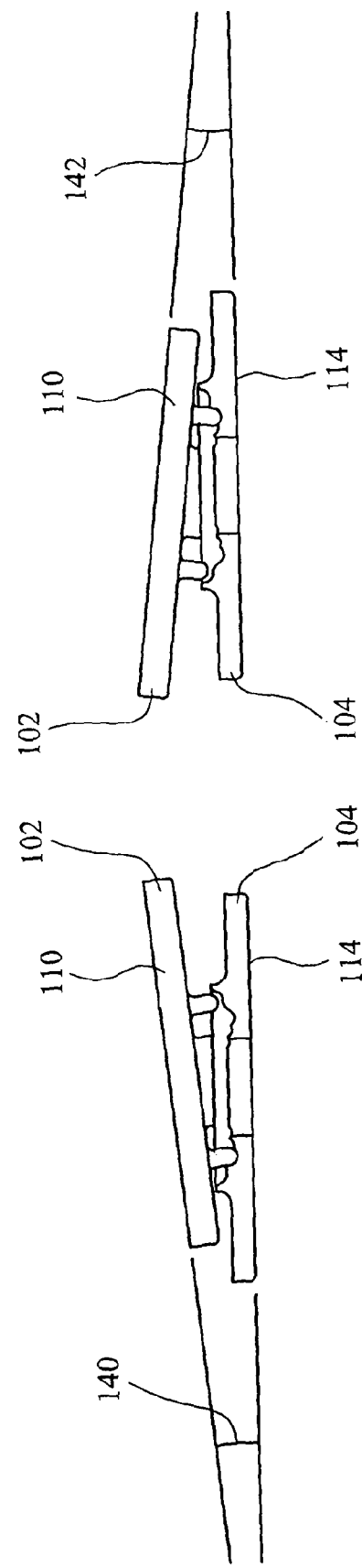
FIG. 6
FIG. 8

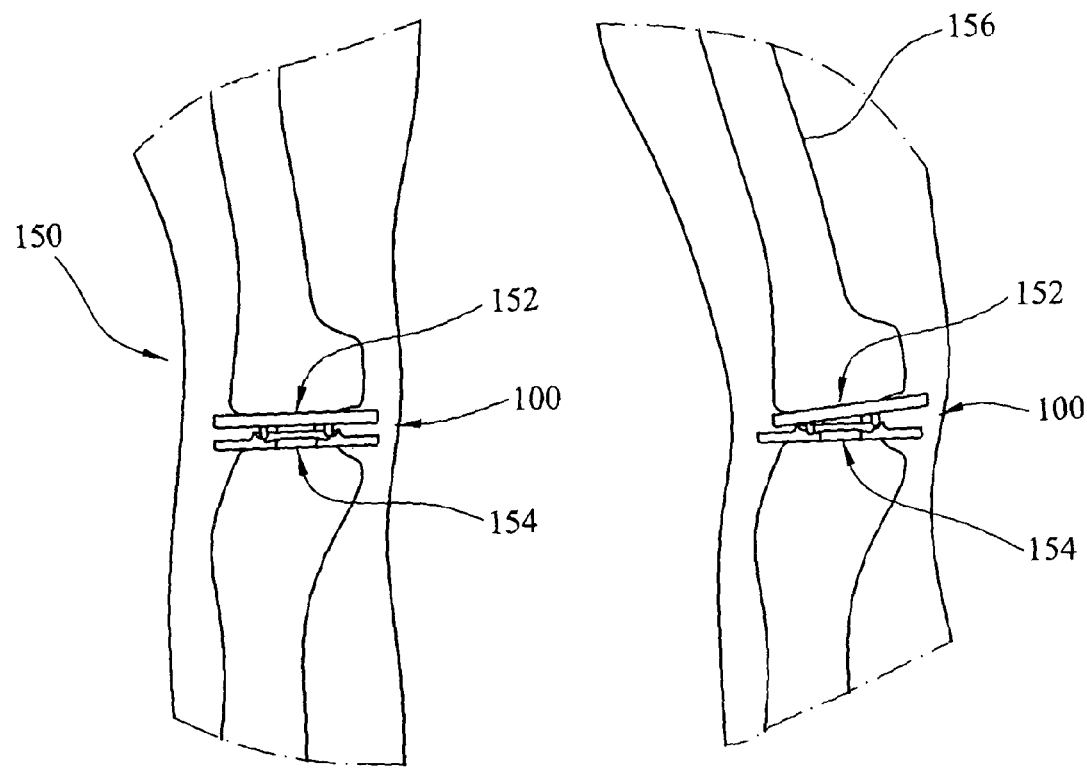
FIG. 9
FIG. 10
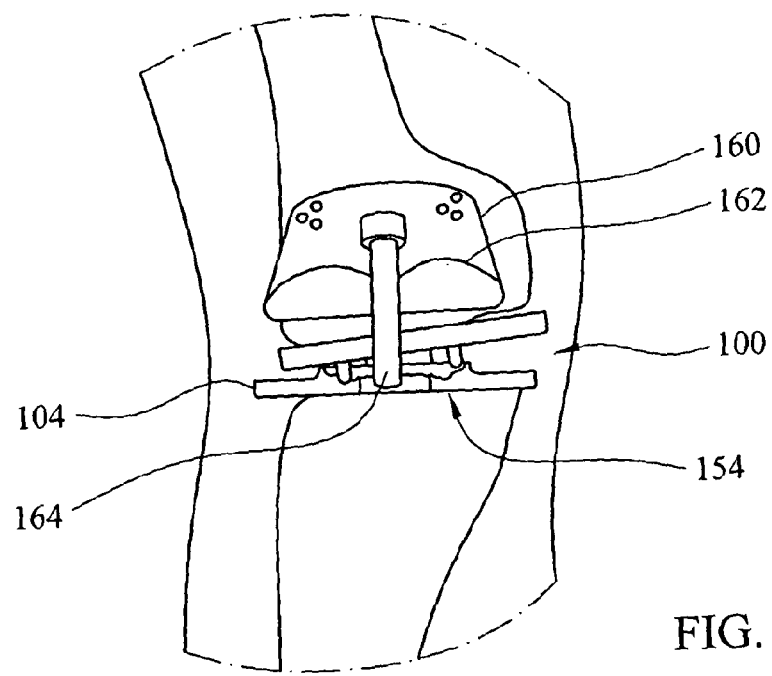
FIG. 11

SURGICAL INSTRUMENT

CROSS REFERENCE TO RELATED APPLICATION

This application is a National Stage 35 U.S.C. 371 of International Patent Application PCT/GB2012/052110, filed Aug. 28, 2012, which claims priority to United Kingdom Application No. GB1115411.9, filed Sep. 7, 2011.

BACKGROUND OF THE INVENTION

The present invention relates to a surgical instrument and methods of use, and in particular to a surgical instrument for, and methods of use in, arthroplasty procedures carried out on the knee joint.

A variety of knee arthroplasty procedures are known. Many involve the use or orthopaedic implants including partial knee procedures, in which only some of the distal part of the femur or proximal part of the tibia are replaced, or total knee procedures in which both the distal part of the femur and the proximal part of the tibia are replaced.

Knee arthroplasty surgical procedures often also involve the soft tissues of the knee joint such as the tendons and ligaments. One example is ligament balancing in which the ligaments around the knee joint are adjusted, often by cutting the individual strands of ligaments themselves and/or releasing their attachments points from the bone, in order to balance the forces exerted by the implant components on each other, or on remaining bone, when the knee joint has been partially or wholly replaced. The balance of the knee joint can be investigated with the leg in flexion and extension to see how the ligaments and knee joint interact over the full likely range of motion of the knee joint.

Ligament balancing is not easy to achieve and outcomes can depend on the skill, judgment and experience of the surgeon. Also, ligament balancing is not entirely reproducible and outcomes can vary depending on the specific anatomy or condition of any patient's joint.

Hence, a successful knee arthroplasty procedure can be dependent on the combination of balance and alignment of the prostheses.

It would therefore be beneficial to provide an instrument and/or surgical methods which can improve the reliability of assessment of ligament balance during a knee arthroplasty procedure and/or the making of cuts or re-cuts to the tibia or femur.

BRIEF SUMMARY OF THE INVENTION

A first aspect of the invention provides an adjustable spacer instrument for use in a knee arthroplasty procedure, comprising: a first member having a substantially planar upper surface; a second member having a substantially planar lower surface; and an angular adjustment mechanism interposed between the first member and the second member, the angular adjustment mechanism being operable to adjust the degree of tilt between the upper surface and the lower surface.

Hence, the spacer instrument can be used to tilt the femur and tibia relative to each other so as to allow the surgeon to assess the balance of the ligaments of the joint and make any adjustments or modifications to the knee arthroplasty procedure.

The angular adjustment mechanism can include a plurality of first formations and a plurality of second formations. The first formations and second formations can have different heights or depths. The first and/or second formations can be repositioned to allow different ones of the first and second formations to interact to cause the first member and second member to change their angular orientation.

The angular adjustment mechanism can be configured to allow the first member and/or second member to pivot about an axis parallel to a plane of the first member or second member. The axis can extend in a generally anterior-posterior direction of the instrument in use.

The angular adjustment mechanism can be configured substantially to maintain the height of the spacer instrument at its centre or along a central axis. Hence, operation of the spacer instrument substantially affects only the degree of tilt of the knee joint and not the degree of separation of the bones or size of the joint gap during surgery.

Preferably, the angular adjustment mechanism includes a releasable lock which can maintain the degree of tilt. Hence, one the degree of inclination has been set by the instrument it is maintained and so the surgeon is free to release the instrument and carry out other acts. The releasable lock can be provided as an integral part of the angular adjustment mechanism. The releasable lock can be provided as a distinct or separate mechanism to the angular adjustment mechanism, and which may be an analogue or continuous adjustment mechanism.

The degree of tilt in two different directions or senses can be adjusted. The direction of tilt can be in the medial direction or the lateral direction.

The angular adjustment mechanism can be operable to continuously adjust the degree of tilt.

The adjustment mechanism can be operable to discretely adjust the degree of tilt. A plurality of different magnitudes of degree of tilt can be provided and/or in two different senses or directions.

The adjustment mechanism can be configured to tilt the upper surface and/or the lower surface about an axis extending in a generally anterior-posterior direction in use.

The adjustment mechanism can comprise entirely integral parts of the first member and/or the second member which interact when the adjustment mechanism is operated. This provides for a compact instrument with a reduced height compared to having the adjustment mechanism made from parts separate to the first and/or second members.

The adjustment mechanism can be provided as a separate or non-integral part of the first and second member. The adjustment mechanism may be operable or configured to adjust the angle without rotating the first and or second part. The adjustment mechanism may be operable or configured to adjust the angle by rotating the whole or a part of the adjustment mechanism relative to both the first and second part. Hence, the first and second members do not need to rotate as the angle they subtend is adjusted.

The adjustment mechanism can be operable by rotating the first member or the second member. The first member can be rotatable relative to the second member or the second member rotatable relative to the first member or the first and second members rotatable relative to each other.

The first member and/or the second member can be rotatable about an axis substantially perpendicular to a plane of the adjustable spacer instrument. The plane can be parallel to the upper or lower surface.

A posterior part of the first member and/or a posterior part of the second member can include a recess configured to accept the posterior cruciate ligament in use. Hence, the posterior cruciate ligament will not be impinged by the instrument in use.

The adjustable spacer instrument can consist of only two parts. This provides improved simplicity of manufacture and compactness of the instrument, particularly its height or thickness. The or each part may be molded or machined. The or each part may be made of a plastics material or a metal. The instrument can be re-useable or disposable.

The adjustment mechanism can comprise a plurality of proud features and a plurality of regions of differing height or depth positioned to engage the proud features in a plurality of different configurations each corresponding to a different degree of tilt between the upper surface and the lower surface. The proud features can be disposed on a lower surface of the first member and the regions of differing height or depth can be disposed on an upper surface of the second member, or vice versa. The proud features and regions or differing height or depth can be arranged in a generally circular pattern or with generally circular rotational symmetry. Preferably at least three proud features and at least three associated or interacting regions of differing height or depth are provided. Three proud features and three interacting regions are the minimal requirement for providing a stable surface in this preferred form of the adjustment mechanism.

The plurality of regions of differing height are in the form of recessed tracks into which the plurality of proud features respectively engage. The recessed tracks can provide races within which the proud features can be constrained to travel.

Each recessed track can include a base. The base can provide a continuous camming surface.

Each recessed track can be in the form of a plurality of detents. Each detent of each track can have a depth arranged to provide a different degree of tilt by magnitude or direction.

The adjustable spacer instrument can further comprise an attachment formation to which a cutting block can be releasably attached. The attachment formation can be a part of the first member or the second member. The attachment formation can be a recess for receiving an attachment formation attached to a cutting block.

The adjustable spacer instrument can have an initial state in which the upper surface and lower surface are parallel and a plurality of tilted states in which the upper surface and lower surface are non-parallel. The adjustable spacer instrument can be driveable between the initial state and the plurality of tilted states by operating the angular adjustment mechanism.

The thickness of the adjustable spacer instrument, when the upper and lower surfaces are parallel can be not greater than 10 mm, and preferably is not greater than 8 mm, and most preferably not greater than 6 mm. The thickness of the spacer instrument can be in the range of approximately 4 mm to 8 mm, preferably about 6 mm. These values provide an instrument particularly suited for use in a joint gap after the tibial or femoral cut has been made, but before the other bone cut has been made.

The thickness of the adjustable spacer instrument, when the upper and lower surfaces are parallel can be not greater than 19 mm, and preferably is not greater than 17 mm, and most preferably not greater than 15 mm. The thickness of the spacer instrument can be in the range of approximately 13 mm to 17 mm, preferably about 15 mm. These values provide an instrument particularly suited for use in a joint gap after the femoral and tibial cuts have been made.

A second aspect of the invention provides a kit of parts, comprising the adjustable spacer instrument of the first aspect of the invention and a cutting block. The cutting block can include a mount with an attachment formation by which the cutting block can be releasably attached to the adjustable spacer instrument. The cutting block can include a cutting guide, the cutting guide being positioned in the cutting block or the cutting block and/or mount being configured so that the cutting guide is parallel to the upper surface or the lower surface of the adjustable spacer instrument.

Hence, the kit of parts can be used to make cuts or re-cuts to the tibia or femur with reference to the upper surface or lower surface of the spacer instrument. This allows parallel resected surfaces of the femur and tibia to be more easily and reliably produced with the knee joint balanced or so as to balance the knee joint.

The mount can be a separate part to the cutting block. The mount can includes an attachment mechanism by which the mount can be releasably attachable to the cutting block. Hence, a conventional cutting block can be used and the mount can be adapted to allow the conventional cutting block to be attached to the spacer instrument.

The mount can be an integral part of the cutting block.

The cutting block can be a femoral cutting block or a tibial cutting block. The femoral cutting block can be for making a distal femoral cut or for making an anterior and/or posterior femoral cut. The tibial cutting block can be for making the proximal tibial cut.

The mount can be adjustable to vary the separation between the cutting guide and the spacer instrument. Hence, the size of the gap between the resected femur and resected tibia can be adjusted. The gap can be a gap in flexion or extension.

A further aspect of the invention provides various methods of carrying out a knee arthroplasty procedure.

The method can comprise resecting the proximal part of the tibia or the distal part of the femur to produce a substantially flat bone surface. An adjustable spacer instrument having an upper surface and a lower surface can be placed on the flat bone surface in a gap between the tibia and the femur. The adjustable spacer instrument can be adjusted vary the degree of tilt between the upper surface and the lower surface. The balance of ligaments of the knee can be assessed.

The adjustable spacer can be locked to maintain the degree of tilt.

Assessment can be carried out by a surgeon or by using a further instrument, such as a pressure or tension sensor or detector.

The method can further comprise attaching a cutting block having a cutting guide to the adjustable spacer instrument. The cutting block can be attached after the joint has been balanced. The cutting guide can be parallel to the upper or lower surface of the adjustable spacer. The cutting guide can be used to resect at least part of the proximal part of the tibia or the distal part of the femur not already resected. Hence, the tibial and femoral cuts can be made parallel with the knee in balance.

Both the proximal part of the tibia and the distal part of the femur can be resected to produce substantially flat bone surfaces. The method can further comprise attaching a cutting block having a cutting guide to the adjustable spacer instrument, wherein the cutting guide is parallel to the upper or lower surface of the adjustable spacer. The cutting guide can be used to re-cut the already resected proximal part of the tibia or the distal part of femur. Hence, previously made cuts can be corrected to make them more parallel when the knee is balanced.

The method can be carried out with the knee in extension or in flexion.

With the knee in flexion, the proximal part of the tibia can have been resected and operating the adjustable spacer instrument can rotate the femur relative to the tibia.

The method can further comprise attaching a cutting block having a cutting guide to the adjustable spacer instrument, wherein the cutting guide is parallel to the lower surface of the adjustable spacer. The cutting guide can be used to resect an anterior part and/or a posterior part of the femur. Hence, the cuts defining the gap in flexion can more reliably be made parallel with the knee in balance.

Embodiments of the invention will now be described in detail, by way of example only, and with reference to the accompanying drawings, in which:

BRIEF DESCRIPTION OF THE DRAWINGS

FIG. 3 shows a schematic front view of the instrument of FIG. 2;

FIG. 4 shows a schematic front view of a further embodiment of an instrument according to the invention;

FIG. 5 shows a schematic perspective view illustrating use of the instrument to adopt a first tilted configuration;

FIG. 6 shows a schematic front view of the instrument as shown in FIG. 5;

FIG. 7 shows a schematic perspective view illustrating use of the instrument to adopt a second tilted configuration FIG. 8 shows a schematic front view of the instrument as shown in FIG. 7;

FIG. 9 shows a schematic front view of the instrument in use in a knee joint in extension during a first embodiment of a method of the invention;

FIG. 10 shows a schematic front view of the instrument further being used in the first embodiment of the method of the invention;

FIG. 11 shows a magnified view of an assembly of a kit of parts according to the invention, including the instrument, and the knee joint as shown in FIG. 10;

Figure 1:
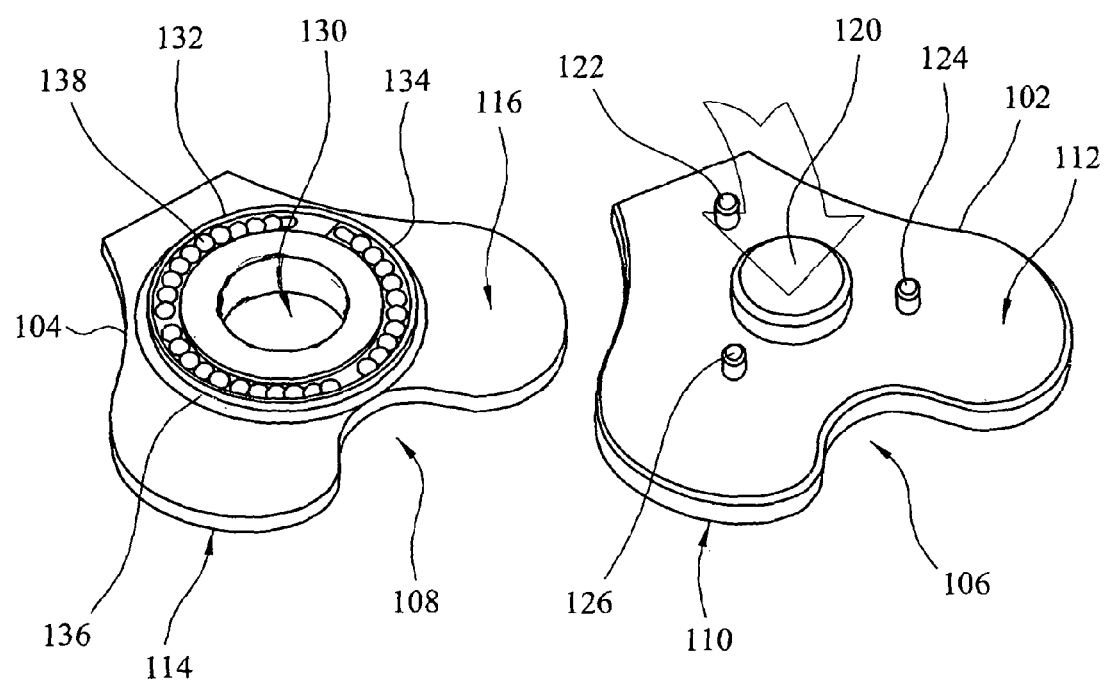
FIG. 1 shows schematic perspective views of the parts of the instrument of the invention in a disassembled state.

Similar items in different Figures share common reference numerals unless indicated otherwise.

DETAILED DESCRIPTION OF THE INVENTION

Figure 2:
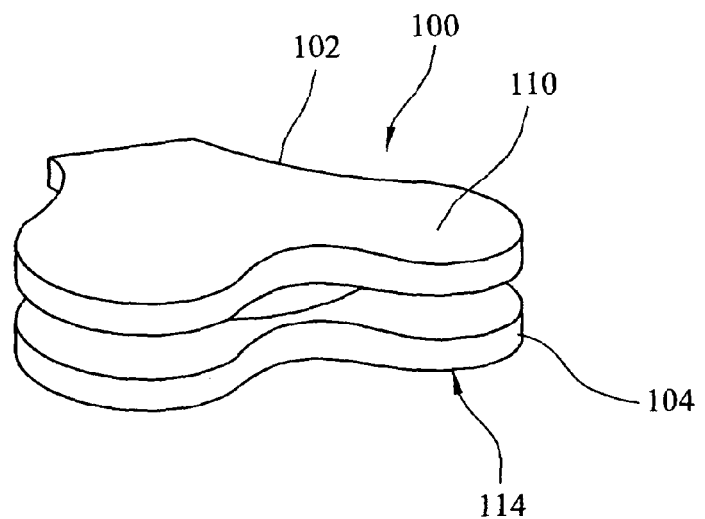
FIG. 2 shows a schematic perspective view of the instrument of FIG. 1 in an assembled state.

With reference to FIGS. 1 and 2, there is shown a first embodiment of a spacer instrument 100 according to the invention. The spacer instrument 100 is used to distract a knee joint during surgery to help a surgeon assess the balance of the knee joint. The spacer instrument 100 includes an angular adjustment mechanism operable to adjust the alignment of the femur and tibia during surgery.

The spacer instrument 100 includes a first top member 102 and a second lower member 104. The top and bottom members each have a generally plate-like form and have a shape similar to that of the proximal part of a tibia. The top plate 102 and bottom plate 104 each generally have a first and second lobe disposed either side of, and defining, a recessed or cutaway portion 106, 108 in a posterior end of the spacer 100. The recess 106, 108 is shaped and configured to accept the posterior cruciate ligament in use and to prevent impingement therewith. The top plate 102 has a substantially flat planar upper surface 110 and a lower surface 112. The bottom plate similarly has a substantially flat planar lower surface 114 and an upper surface 116.

The top plate 102 has a centrally positioned circular boss 120 extending from its lower surface 112. Three dome-tipped pegs 122, 124, 126 also extend from the lower surface 112 and are disposed in a generally equilateral manner about central boss 120. Each of pegs 122, 124, 126 has the same height, that is extends by the same distance from the lower surface 112. Pegs 122, 124, 126 provide a part of the angular adjustment mechanism of the adjustable spacer.

A circular aperture 130 is located from the centre of the lower plate 104. Aperture 130 is dimensioned to accept boss 120 therein. First, second and third recessed tracks 132, 134, 136 are disposed in arcs concentric to central aperture 130. Each track 132, 134, 136 is provided in the form of a plurality of detents. In the illustrated embodiment, there are eleven distinct detents in each track.

Each detent in a track has a different depth, while corresponding detents in the different tracks have the same depth. The middle detent, e.g. detent 138, corresponds to a zero degree of tilt between the upper surface 110 and lower surface 114 of the top and bottom members as illustrated in FIG. 2. The depth of the detents either side of the middle detent gradually increases to provide differing degrees of tilt in different directions. The detents either side of the central detent each respectively provide +/−1°, the next detent +/−3°, the next detent +/−5°, the next detent +/−7° and the final detent +/−9°.

When assembled, as illustrated in FIGS. 2 and 3, boss 120 is received in aperture 130 and each peg 122, 124, 126 is received in a respective one of the tracks 132, 134, 136. With the top and bottom plates in registration, as illustrated in FIG. 2, each peg is located within the middle detent of each track. As the middle detent of each track has the same depth, and the pegs each have the same height, the upper 110 surface of the top plate 102 is parallel to the lower surface 114 of the bottom plate 104, as illustrated in FIGS. 2 and 3. In this configuration, the height, that is the thickness of the spacer from the upper surface 110 to the lower surface 114, is approximately 6 mm. As illustrated in FIGS. 5 to 8, by rotating the top and bottom plates relative to each other about boss 120, pegs 122, 124, 126 occupy a different set of three detents whose depths are arranged to cause a degree of tilt between upper surface 110 and lower surface 114. For example, by rotating top plate 102 relative to bottom plate 104 in a first direction about boss 120, pegs 122, 124, 126 travel around tracks 132, 134, 136 and occupy detents at heights causing a degree of tilt 140 of 5°, as illustrated in FIG. 6. Alternatively, by rotating top plate 102 relative to bottom plate 104 in the opposite sense, as illustrated in FIG. 7, the top surface 110 can be tilted relative to the bottom surface 114 by angle 142 also of 5°, but in an opposite sense. Each group of three detents is calibrated so as to define a plane at a predefined angle of tilt and with a predefined sense. By rotating the top surface relative to the bottom surface, the pegs can be repositioned so as to engage with the different groups of detents so as to vary the degree of tilt between the upper surface 110 and lower surface 114. In the illustrated embodiment, the detent depths are configured so as to provide tilt angles of 0°, +/−1°, +/−3°, +/−5°, +/−7° and +/−9°.

Further, the use of detents and round headed pegs provides a releasable locking mechanism by which the base of instrument 100 can have a degree of tilt of the upper surface 110 and lower surface 114 fixed. The detents prevent the pegs from easily moving into an adjoining detent when the spacer instrument is under compression in use. Therefore, there is a threshold rotation force which must be applied to the top plate in order to rotate the top plate relative to the bottom plate so as to adjust the degree of tilt of the upper and lower surfaces.

Further, the discrete detents allow the adjustment mechanism to have discrete, or non-continuous, adjustment of the degree of tilt.

Furthermore, the detents do not need to provide a smooth transition and therefore can be arranged to provide whatever magnitude or sense of angle might be useful, and also whatever sequence of angles might be useful in the spacer instrument. Each group of three detents can affect a completely different angle change. For example, the detents could be configured to provide angles of +/−1°, +/−2°, +/−3°, +/−6°, +/−9° and +/−30°.

In alternative embodiments, the detents can be replaced by a smooth base surface of the trough providing a continuous camming surface while in continuous adjustment of the degree of tilt. However, in such embodiments, a separate locking mechanism would need to be provided in order to releasably lock the degree of tilt. Further, the camming surface would need to provide a gradual change in angle and may not be able to accommodate as large tilt angle changes as the use of discrete detents.

The combination of angles provided by the detents can of course be varied to provide the magnitude and range of angles required for any particular application.

In an alternate embodiment of the adjustment mechanism, a part of the adjustment mechanism can be provided wholly separately from the first and second members. A separate rotatable angle adjustment part providing either detents on both its upper and lower surfaces or protrusion on both surfaces, is sandwiched between the co-operating features (i.e. protrusions or detents) on the upper and lower surfaces of the members. Hence, this rotatable angle adjustment part can be rotated to adjust the angle between the members while the members themselves do not rotate, but merely tilt.

The diameter of boss 120 and circular aperture 130 are selected so as to allow the top plate 102 to pivot relative to the bottom plate 104. Boss 120 allows the top plate to be rotated relative to the bottom plate about an axis essentially perpendicular to the plane of the bottom plate and also helps to prevent pegs 122, 124, 126 escaping from their respective tracks 132, 134, 136, during operation of the spacer instrument.

FIG. 4 shows a further embodiment of the spacer instrument 100 similar to the first embodiment. The further embodiment includes a first recess 144 and a second recess 146 in the anterior of the instrument. Recess 144 and 146 provide formations to which a mount for a cutting block can be reasonably attached to the spacer instrument 100 during use.

Additionally or alternatively, in other embodiments, the upper surface 110 or lower surface 114 can include formations for allowing shim components to be attached to the lower surface 114 or upper surface 110 so as to increase the overall thickness of the instrument during use. Preferably, the formations allow releasable attachment of the shim or shims so as to allow the thickness of the spacer instrument 100 to be adjusted, depending on the size of the gap in the patient's knee between the femur and tibia or the amount of distraction desired between the patient's femur and tibia.

As illustrated in FIG. 1, the spacer instrument has a very simple construction and consists of only two separate parts or pieces. There are no sub-parts and the parts of the angular adjustment mechanism are wholly provided by integral parts of the top and bottom plates. This provides a simple and efficient to manufacture instrument. For example, the instrument may be made from a reinforced polymer, such as fibre reinforced nylon and could be moulded from such plastics and similar materials. When made from plastics materials, the instrument could be provided as a single use, disposable instrument. The instrument could also be made from a machined metal or allow, such as surgical grade stainless steel, when provided as a reusable instrument.

Further, by providing the components of the angular adjustment mechanism as integral parts of the top and bottom plates, rather than separate parts, the overall thickness of the instrument can be reduced. The gap between the un-cut femur and resected tibia of a typical knee is of order 10 mm and so there is particularly little space in which to insert the instrument in use and so the instrument needs to be of low thickness. Similarly, the gap between the resected femur and un-cut tibia is of order 10 mm and so a low thickness instrument is required for such surgical approaches.

The spacer instrument is easy and versatile to use intra-operatively. The same instrument allows for re-cuts to correct imbalance of the knee and also allows for initial setting of the distal cut angle, femur rotation, extension gap and flexing gap depending on the surgical procedure adopted.

Having described construction and operation of the spacer instrument 100, a variety of surgical procedures in which it can be used will now be described. Broadly speaking, the spacer instrument has two main modes of use. A first mode of use is pre-final cut with the knee joint either in flexion or extension. The second main mode of use is post-final cut to allow fine tuning of the knee, in flexion or extension, in order to optimise balance of the knee. The instrument is designed to compliment ligament release techniques, or to eliminate the need for them, by altering the bone cuts instead to compliment the patient's current or existing ligaments. Hence, the instrument allows a surgical approach based on altering the bone cuts which is believed to be easier than selectively cutting ligament fibres.

Various methods of use of the spacer instrument with the patient's leg in extension, will now be described with reference to FIGS. 9 to 11. Initially, the proximal tibial cut and distal femoral cut are made resulting in substantially flat resected bone surfaces on the distal end of the femur and proximal end of the tibia. This results in a joint space of approximately 19 mm thickness. The spacer instrument 100 is provided in its initial, 0° of tilt configuration (i.e. with the upper and lower surfaces parallel) and is inserted into the joint space. FIG. 9 shows a schematic view of a leg 150 of a patient adjacent to the patient's knee joint. FIG. 9 also shows the spacer instrument 100 located in the joint space with the upper surface of the top plate and lower surface of the joint plate generally parallel and contacting the resected femur 152 and tibia 154 bone surfaces respectively. With the spacer instrument 100 in its initial parallel configuration, the surgeon can assess the tension in the ligaments surrounding the knee joint with the instrument in its parallel configuration. Ideally, with the knee in balance, the resected surfaces of the tibia and femur should be parallel and define a "rectangular" space into which the prosthetic components can be implanted. If the knee joint is not in tension, because the joint space is larger than the thickness of the spacer instrument, then shims can be added to the spacer instrument, as described above, in order to increase its thickness in the parallel configuration. Once any shims have been added, the surgeon can further assess the tension in the ligaments surrounding the knee joint.

If, following assessment of the ligaments, the surgeon determines that with these initial cuts, the knee is not sufficiently balanced, then two courses of action are available.

The surgeon can release the knee ligaments, by making cuts to the fibres of the ligaments, or to the positions at which the ligaments are attached to the bone, until the surgeon considers the knee to be balanced.

Alternatively, as illustrated in FIG. 10, the surgeon can operate the spacer instrument 100 by twisting the top plate relative to the bottom plate so as to adjust the angle of inclination of the upper and lower surfaces of the spacer instrument. This is illustrated in FIG. 10, in which the femur 156 has tilted in a generally lateral direction about a pivoting axis generally in the anterior posterior direction. The surgeon manipulates the top plate to rotate it relative to the bottom plate, about an axis of rotation substantially perpendicular to the plane of the bottom plate. The angle of tilt, or inclination, of the upper surface relative to the lower surface can be adjusted until the surgeon assesses the ligaments to be balanced. As discussed above, the action of the pegs and the detents, under tension exerted by the knee joint, causes the spacer instrument to be reasonably locked at this angle of relative tilt of the upper and lower surfaces. With the ligaments now balanced, with the knee joint in this new configuration, the distal resected surface of the femur 152 is no longer parallel to the resected proximal surface 154 of the tibia. Hence, the distal portion of the femur is next recut so as to be parallel to the resected surface of the tibia 154.

As illustrated in FIG. 11, a distal cutting block 160 including a cutting guide 162 is releasably attached to the spacer instrument 100 by a mount 164. Mount 164 is releasably attached to attachment formation of the bottom plate 104. The cutting block 160 and mount 164 are configured such that the cutting guide 162 of the cutting block 160 lies in a plane parallel to the lower surface of the bottom plate 104. Hence, the cutting guide is maintained parallel to the resected tibial surface 154 and allows the femur to be recut such that the further resected distal femoral surface will be parallel to the tibial resected surface with the knee ligaments in balance.

The mount 164 can include an adjustment mechanism allowing the height of the cutting block 160 to be adjusted so as to allow the gap between the femoral cut and tibial cut to be adjusted. Also, a scale can be provided on the mount 164 so as to display a measure of the gap depending on the depth of femoral cut made.

In a further embodiment of a method of use of the spacer instrument, also with the knee joint in extension, the spacer instrument 100 can be used prior to the distal femoral cut being made, so as to set the angle of the knee and depth of the distal cut. Initially, only the proximal tibial cut is made, then the spacer instrument is introduced into the joint space in its parallel configuration with the condyles of the femur engaging the upper surface of the top plate 102. Any shims can be added if needed in order to place the joint in tension. The surgeon can then assess the balance of the ligaments and operate the spacer instrument 100 in order to tilt the upper surface relative to the lower surface so as to determine the angle of the knee joint providing better ligament balance.

Then, with the knee joint angle set, the distal cutting block 160 is attached to the tibial plate 104 of the instrument, similarly to as illustrated in FIG. 11, and the depth of the distal cut set by adjusting the height of the cutting block 160 relative to the tibial plate 104 before the distal femoral cut is made. Hence, the resected proximal tibial surface and distal femoral surface should be generally parallel and with the ligaments generally in balance.

In a further alternative embodiment with the knee joint in extension, a similar approach can be used to that described immediately above, but in which only the distal femoral cut is made initially and then the proximal tibial cut is made with reference to the upper surface of the top plate 102, by attaching a tibial cutting block via a mount attached to the top plate 102. Hence again, the resected tibial and femoral surfaces can be provided generally parallel to each other with the ligaments in balance.

Figure 12:
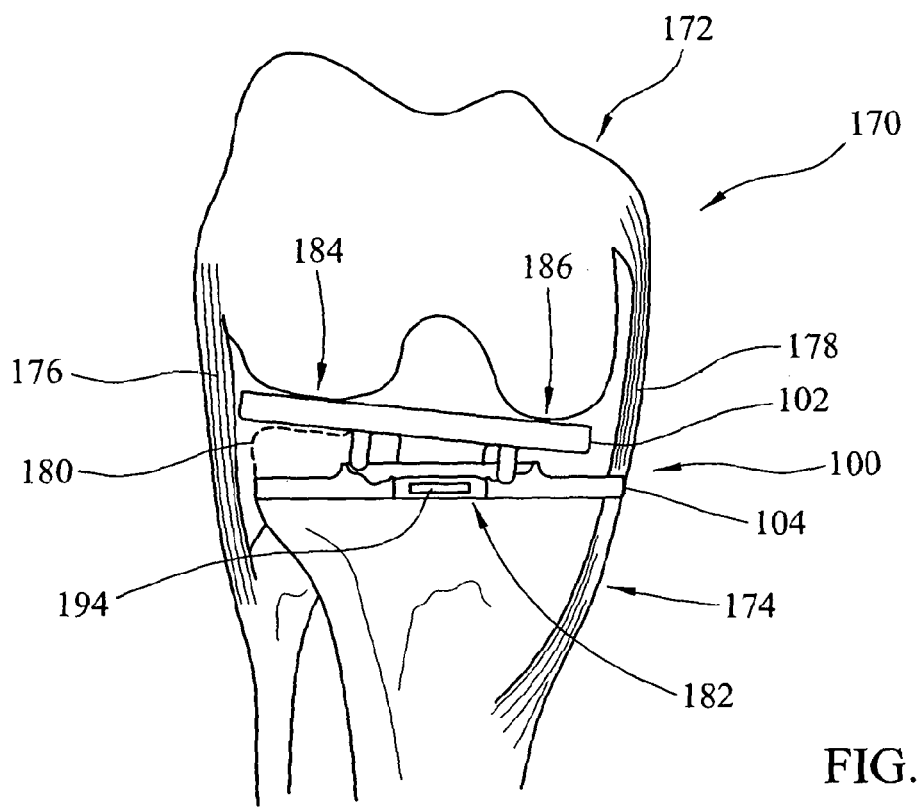
FIG. 12 shows a schematic front view of the instrument in use in a knee joint in flexion during a second embodiment of a method of the invention.
Figure 13:
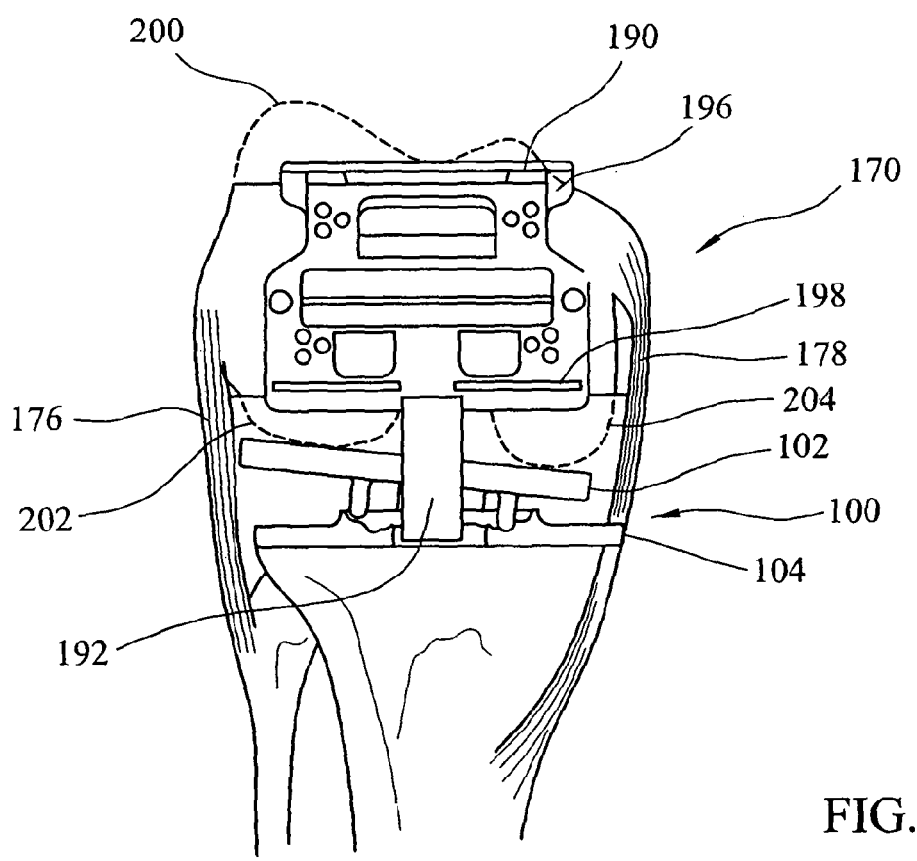
FIG. 13 shows a schematic front view of an assembly of a kit of parts according to the invention, including the instrument, and further being used in the second embodiment of the method of the invention.

Methods of use of the spacer instrument 100 with the knee joint in flexion according to embodiments of the invention will now also be described. With reference to FIGS. 12 and 13, there is shown a knee joint 170 of a patient in flexion. The knee joint comprises the distal part of the femur 172 and the proximal part of the tibia 174. Medial and lateral parts of the knee ligaments 176, 178 are also shown in FIG. 12.

Initially, the proximal tibial cut is made to remove the proximal portion of the tibia, as illustrated by dashed line 180 and resulting in a substantially flat resected proximal tibial surface 182. The spacer instrument 100 is inserted into the joint gap in its parallel configuration with the lower surface of the bottom plate 104 resting on the resected tibial surface 182. The upper surface of the top plate 102 rests against the posterior portions of the condyles 184, 186 of the femur.

The spacer instrument 100 is operated by the surgeon by rotating the top plate relative to the bottom plate so as to incline the upper surface of the top plate relative to the lower surface of the bottom plate. The surgeon operates the spacer instrument until the femur is directly rotated relative to the tibia and such that the ligaments 176, 178 are tensioned equally. The assessment of the tension of the ligaments 176, 178 can be made manually by the surgeon or through use of a pressure sensing device so as to determine the balance of the pressure exerted by the instrument 100 on the tibia. Once the degree of tilt of the spacer instrument 100 has been settled upon, the spacer instrument automatically locks to that degree of tilt, through the interaction of the pegs and detents. A cutting block 190 is then connected to the spacer instrument 100 by a mount 192 which releasably engages with an attachment feature 194 of the tibial plate 104. The cutting block 190 includes a first cutting guide 196 for making an anterior cut to the femur and a second cutting guide 198 for making a posterior cut to the femur (and also cutting guides for making anterior and posterior chamfer cuts). The mount 192 can be adjustable in height so as to vary the height of the posterior cut so as to set the size of the flexion gap. The mount 192 can also include a scale to provide a measure of the flexion gap that would be provided by different posterior cut heights. The cutting block 190 and mount 192 are configured such that the first cutting guide 196 and second cutting guide 198 each lies in a plane generally parallel to the plane of the lower surface of the bottom plate 104. Hence, the surgeon can make the anterior cut to remove the anterior portion of the femur, as illustrated by dashed line 200 using the first cutting guide and may also make the posterior cuts using the second cutting guide 198 to remove the posterior parts of the condyles, illustrated by dashed lines 202 and 204. Hence, the cutting block allows the anterior and posterior cuts to be made parallel to the initial tibial cut so as to produce a rectangular flexion gap.

Hence, the instrument and method embody the general concept of altering the alignment of the bones so as to achieve balanced ligaments rather than balancing the ligaments relative to a predetermined alignment. The surgical instrument 100 can be used to allow a measured technique or a balanced technique. In a measured technique, the angle of inclination of the spacer instrument can be set, e.g. to 3°, in order to check the balance of the knee joint at that specific angle. For example, a surgeon may determine that they consider a 3° angle to be appropriate and use the spacer instrument to create the 3° angle in the knee joint and then make cuts to the femur or tibia for that angle.

Alternatively, in the balanced technique, the instrument can be operated in situ in order to determine the angle which the ligaments are generally in balance. The cuts to the tibia or femur can then be made for the angle determined to provide balance of the ligaments.

Hence, the instrument of the invention allows for recutting of previously made cuts in order to correct imbalance, allows for the initial setting of the distal cut angle, femoral rotation, extension gap and correction gap. Hence, a wide variety of surgical techniques are possible using the angle adjustable spacer instrument of the invention.

It will be appreciated that while operation of the instrument by rotating the top plate relative to the lower plate has been described, the instrument may also be operated by rotating the bottom plate relative to the top plate, which remains substantially fixed. Additionally, or alternatively, both the top plate and bottom plate can be rotated in order to operate the instrument. It will also be appreciated that the instrument operates by allowing the angle between the upper surface of the top plate and the lower surface of the bottom plate to be adjusted. Whether the top plate tilts relative to the bottom plate, the bottom plate tilts relative to the top plate or the plates tilt relative to each other, is not material.

Various modifications and variations will be apparent to a person of ordinary skill in the art from the above discussion of the invention.

The invention claimed is:

1. An adjustable spacer instrument for use in a knee arthroplasty procedure, comprising:
   a first member having a substantially planar upper surface;
   a second member having a substantially planar lower surface; and
   an angular adjustment mechanism interposed between the first member and the second member, the angular adjustment mechanism being operable to adjust the degree of tilt between the upper surface and the lower surface and including a releasable lock which can maintain the degree of tilt,
   wherein the adjustment mechanism comprises a plurality of proud features and a plurality of regions of differing height positioned to engage the proud features in a plurality of different configurations each corresponding to a different degree of tilt between the upper surface and the lower surface.

2. The adjustable spacer instrument of claim 1, wherein the angular adjustment mechanism is operable to continuously adjust the degree of tilt.

3. The adjustable spacer instrument of claim 1, wherein the adjustment mechanism is operable to discretely adjust the degree of tilt.

4. The adjustable spacer instrument of claim 1, wherein the adjustment mechanism is configured to tilt the upper surface and/or the lower surface about an axis extending in a generally anterior-posterior direction in use.

5. The adjustable spacer instrument of claim 1, wherein the adjustment mechanism comprises entirely integral parts of the first member and the second member which interact when the adjustment mechanism is operated.

6. The adjustable spacer instrument of claim 1, wherein the adjustment mechanism is operable by rotating the first member or the second member relative to each other.

7. The adjustable spacer instrument of claim 1, wherein the first member or the second member are rotatable about an axis substantially perpendicular to a plane of the adjustable spacer instrument.

8. The adjustable spacer instrument of claim 1 wherein a posterior part of the first member and/or a posterior part of the second member includes a recess configured to accept the posterior cruciate ligament in use.

9. The adjustable spacer instrument of claim 1, wherein the adjustable spacer instrument consists of only two parts.

10. The adjustable spacer instrument of claim 1, wherein the adjustment mechanism includes a rotatable part separate to the first member and the second member, and wherein the rotatable part is operable to adjust the degree if tilt, without the first and/or second members rotating.

11. The adjustable spacer instrument of claim 1, wherein the plurality of regions of differing height are in the form of recessed tracks into which the plurality of proud features respectively engage.

12. The adjustable spacer instrument of claim 11, wherein each recessed track includes a base providing a continuous camming surface.

13. The adjustable spacer instrument of claim 11, wherein each recessed track is in the form of a plurality of detents.

14. The adjustable spacer instrument of claim 1, and further comprising an attachment formation to which a cutting block can be directly or indirectly releasably attached.

15. The adjustable spacer instrument of claim 1, wherein the adjustable spacer instrument has an initial state in which the upper surface and lower surface are parallel and a plurality of tilted states in which the upper surface and lower surface are non-parallel and the adjustable spacer instrument is driveable between the initial state and the plurality of tilted states by operating the angular adjustment mechanism.

16. A adjustable spacer instrument of claim 1, wherein the thickness of the adjustable spacer instrument, when the upper and lower surfaces are parallel is not greater than 20 mm.

17. A kit of parts comprising:
   the adjustable spacer instrument of claim 14; and
   a cutting block, wherein the cutting block includes a mount with an attachment formation by which the cutting block can be releasably attached to the adjustable spacer instrument and wherein the cutting block includes a cutting guide, the cutting guide being positioned in the cutting block so as to be parallel to the upper surface or the lower surface of the adjustable spacer instrument.

18. The kit of parts of claim 17, wherein the mount is a separate part to the cutting block and includes an attachment mechanism by which the mount is releasably attachable to the cutting block.

19. The kit of parts of claim 17, wherein the mount is an integral part of the cutting block.

20. The kit of parts of claim 17, wherein the mount is adjustable to vary the separation between the cutting guide and the spacer instrument.

* * * * *